United States Patent
Bader et al.

(10) Patent No.: US 10,472,608 B2
(45) Date of Patent: Nov. 12, 2019

(54) GENERATION OF A MESENCHYMAL STROMAL CELL BANK FROM THE POOLED MONONUCLEAR CELLS OF MULTIPLE BONE MARROW DONORS

(71) Applicants: Johann Wolfgang Goethe-Universität, Frankfurt Am Main, Frankfurt am Main (DE); DRK BLUTSPENDEDIENST BADEN-WÜRTTEMBERG-HESSEN GGMBH, Frankfurt am Main (DE)

(72) Inventors: Peter Bader, Dreieich (DE); Selim Kuci, Frankfurt am Main (DE); Zyrafete Kuci, Frankfurt am Main (DE); Halvard Bönig, Frankfurt (DE)

(73) Assignees: JOHANN WOLFGANG GOETHE—UNIVERSITÄT, Frankfurt am Main (DE); DRK BLUTSPENDEDIENST BADEN-WÜRTTEMBERG-HESSEN GGMBH, Frankfurt am Main (DE)

( * ) Notice: Subject to any disclaimer, the term of this patent is extended or adjusted under 35 U.S.C. 154(b) by 0 days.

(21) Appl. No.: 15/326,213

(22) PCT Filed: Jul. 14, 2015

(86) PCT No.: PCT/EP2015/066083
§ 371 (c)(1),
(2) Date: Jan. 13, 2017

(87) PCT Pub. No.: WO2016/008895
PCT Pub. Date: Jan. 21, 2016

(65) Prior Publication Data
US 2017/0198257 A1  Jul. 13, 2017

(30) Foreign Application Priority Data
Jul. 16, 2014 (EP) .................................. 14177312

(51) Int. Cl.
*C12N 5/0775* (2010.01)
*A61K 35/28* (2015.01)
*C12Q 1/6881* (2018.01)
*A61K 35/12* (2015.01)

(52) U.S. Cl.
CPC ............ *C12N 5/0663* (2013.01); *A61K 35/28* (2013.01); *C12Q 1/6881* (2013.01); *A61K 2035/124* (2013.01)

(58) Field of Classification Search
CPC .... C12N 5/0663; C12Q 1/6881; A61K 35/28; A61K 2035/124
See application file for complete search history.

(56) References Cited

U.S. PATENT DOCUMENTS 5,486,359 A   1/1996   Caplan et al.
2012/0087933 A1   4/2012   Tom et al.

FOREIGN PATENT DOCUMENTS

WO   WO 2011/064733   6/2011
WO   WO 2012/048093   4/2012

OTHER PUBLICATIONS

Bernardo et al. Human Bone Marrow-Derived Mesenchymal Stem Cells Do Not Undergo Transformation after Long-term in vitro Culture and Do Not Exhibit Telomere Maintenance Mechanisms. Cancer Res 2007;67(19):9142-9 (Year: 2007).*
Samuelsson et al. Optimizing in vitro conditions for immunomodulation and expansion of mesenchymal stromal cells. Cytotherapy (2009) vol. 11, No. 2, 129-136 (Year: 2009).*
Bergfeld et al. Bone Marrow-Derived Mesenchymal Stromal Cells Promote Survival and Drug Resistance in Tumor Cells. Mol Cancer Ther; 13(4); 962-75. (Year: 2014).*
Notification Concerning Transmittal of International Preliminary Report on Patentability, International Application No. PCT/EP2015/066083, entitled "Generation of a Mesenchymal Stromal Cell Bank From the Pooled Mononuclear Cells of Multiple Bone Marrow Donors", dated Jan. 26, 2017.
Cooper et al., "Establishment of a Mesenchymal Stem Cell Bank", *Stem Cells International*, 108:10:792-798 (2011).
Dal Pozzo et al., "High Recovery of Mesenchymal Progenitor Cells with Non-Density Gradient Separation of Human Bone Marrow", *Cytotherapy*, 12:5:579-586 (2010).
Notification of Transmittal of the International Search Report and the Written Opinion of the International Searching Authority, International Application No. PCT/EP2015/066083, entitled "Generation of a Mesenchymal Stromal Cell Bank From the Pooled Mononuclear Cells of Multiple Bone Marrow Donors", dated Sep. 25, 2015.

(Continued)

*Primary Examiner* — Taeyoon Kim
(74) *Attorney, Agent, or Firm* — Saul Ewing Arnstein & Lehr LLP; Mary K. Murray

(57) ABSTRACT

The present invention pertains to an improved mesenchymal stromal cell (MSC) preparation and a method for producing the same. The invention provides a new strategy to isolate MSC from bone marrow mononuclear cells (BM-MNCs) by pooling BM-MNCs of multiple unrelated (third-party) bone marrow donors. The MSC preparation manufactured in accordance with the methodology of the invention is characterized by a stable proliferative capability and an increased immunosuppressive potential when compared to individual donor MSC preparations or a pool of individual MSCs generated from multiple donors. The MSCs prepared ac- cording to the invention are particularly useful for medical applications such as the treatment of graft-versus-host disease (GvHD) in recipients with hematopoietic stem cell transplants, patients with autoimmune disorders and as a cell-based therapy in regenerative medicine.

15 Claims, 8 Drawing Sheets

(56) References Cited

OTHER PUBLICATIONS

Figure 1:
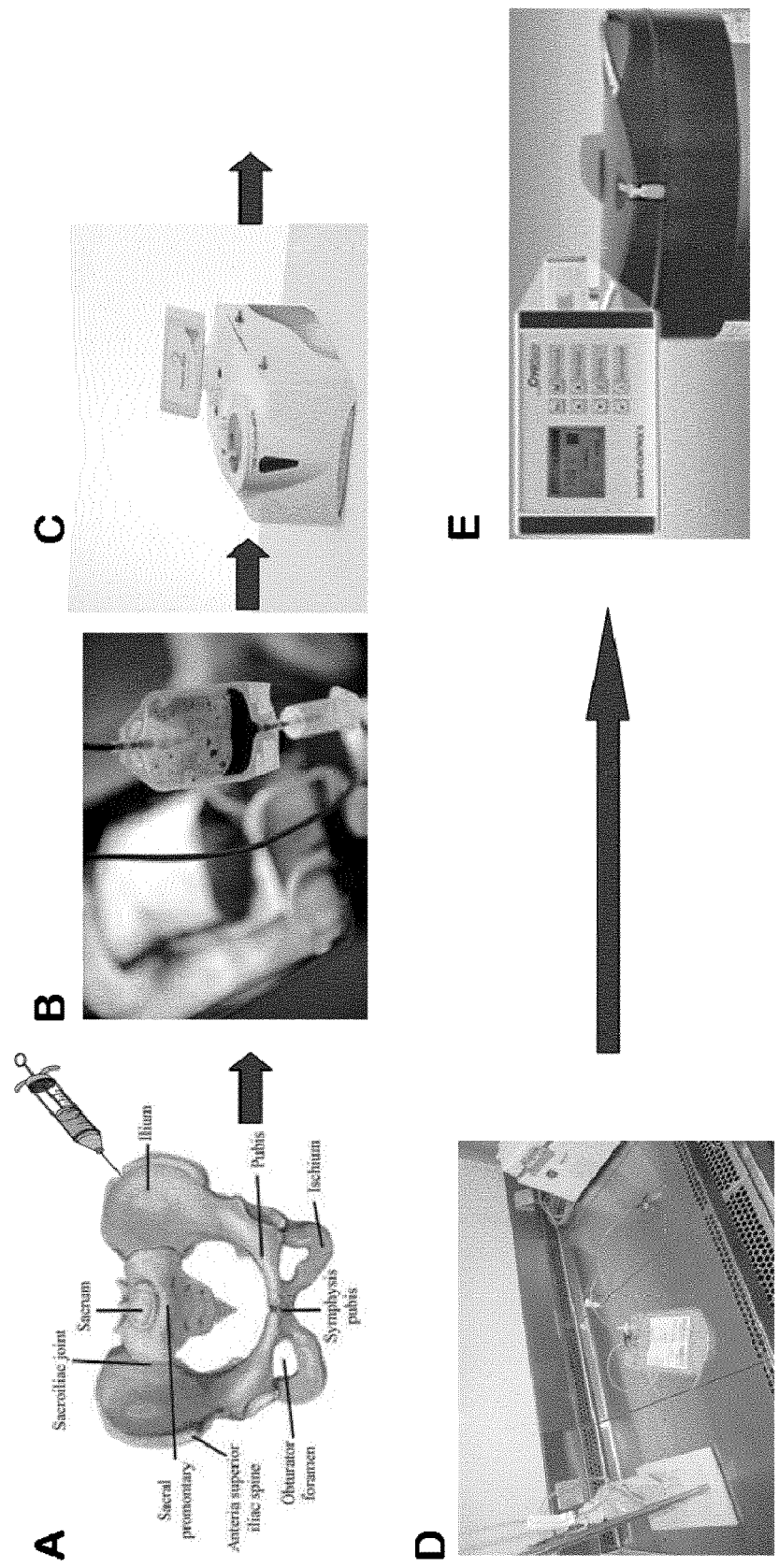

Ringden et al., "Pooled MSCs for Treatment of Severe Hemorrhage", *Bone Marrow Transplantation*, 46:8:1158-1160 (2011).
Thirumala et al., "Manufacturing and Banking of Mesenchymal Stem Cells", *Expert Opinion on Biological Therapy*, 13:5:673-691 (2013).

* cited by examiner

GENERATION OF A MESENCHYMAL STROMAL CELL BANK FROM THE POOLED MONONUCLEAR CELLS OF MULTIPLE BONE MARROW DONORS

RELATED APPLICATIONS

This application is the U.S. National Stage of International Application No. PCT/EP2015/066083, filed Jul. 14, 2015, which designates the U.S., published in English, and claims priority under 35 U.S.C. §§ 119 or 365(c) to European Application No. 14177312.7, filed on Jul. 16, 2014. The entire teachings of the above applications are incorporated herein by reference.

FIELD OF THE INVENTION

The present invention pertains to an improved mesenchymal stromal cell (MSC) preparation and a method for producing the same. The invention provides a new strategy to isolate MSC from bone marrow mononuclear cells (BM-MNCs) by pooling BM-MNCs of multiple unrelated (third-party) bone marrow donors. The MSC preparation manufactured in accordance with the methodology of the invention is characterized by a stable proliferative capability and an increased immunosuppressive potential when compared to individual donor MSC preparations or a pool of individual MSCs generated from multiple donors. The MSCs prepared according to the invention are particularly useful for medical applications such as the treatment of graft-versus-host disease (GvHD) in recipients with hematopoietic stem cell transplants, patients with autoimmune disorders and as a cell-based therapy in regenerative medicine.

DESCRIPTION

Mesenchymal stromal cells (MSCs) since their discovery in the 1970s by Friedenstein et al. have been extensively investigated concerning their immunomodulatory and regenerative potential both in vitro and in vivo. In the last decade, considerable progress has been made in elucidating the pleiotropic function of MSCs despite the lack of a unique cell surface marker for their identification and prospective isolation. In order to allow for a comparison of the effect of clinically used MSCs from different manufacturers, the International Society for Cellular Therapy proposed a set of phenotypic and functional criteria to define MSCs. The absence of HLA-class II antigens and co-stimulatory molecules on the surface of MSCs, paracrine secretion of a vast array of molecules with immunomodulatory potential, as well as the ease of their prospective isolation from many tissues, makes them a very attractive source for cell-based therapeutic strategies in a wide range of clinical conditions such as tissue injuries, inflammation processes and autoimmune disorders. However, for all these clinical applications there is a need of having at the right moment a large number of the "off-the-shelf" MSCs.

To date, the majority of clinical research was performed using mesenchymal stromal cells (MSCs) generated from a single bone marrow donor. As the effects of MSC preparations vary markedly from donor to donor, the results obtained from these studies were to a large extent very heterogeneous. In addition, the inventors and others have demonstrated that MSCs exhibit not only a vast donor-to-donor but also intrapopulation heterogeneity at the clonal level. This remarkable heterogeneity poses the major obstacle in the development of clinical manufacturing protocols, which could be used to reproducibly generate MSC-products with an equivalent therapeutic potency.

An isolation process for human mesenchymal stromal cells from bone marrow samples is described in U.S. Pat. No. 5,486,359. An antibody binding to mesenchymal stromal cells was developed in order to purify MSCs from bone marrow aspirates or ground bone material. The bone marrow samples are separated via a Ficoll gradient and the low density fraction is used for stem cell isolation. U.S. Pat. No. 5,486,359 cultured the cells in normal medium for 1 day on tissue culture plastic to allow stem cells to adhere. Thereafter, the medium is exchanged and the cells are cultured until confluent with medium exchanges every 4 days to obtain the MSCs.

WO 2012/048093 discloses the isolation of bone marrow derived MSCs from single donors. WO 2012/048093 teaches that MSC preparations derived from a single donor can be expanded to clinical scale preparations.

Pooling of MSC preparations after their generation from the individual bone marrow mononuclear cell fractions of unrelated bone marrow donors or bone samples is known to be possible for the treatment of life-threatening haemorrhage in a patient with myelofibrosis who underwent allogeneic hematopoietic stem cell transplantation (O Ringdén and K LeBlanc, Bone Marrow Transplantation, 2011; 46:1158-1160). In this study, clinical-grade MSC preparations derived from two different donors separately were combined to increase the likelihood of response.

In view of the above described prior art, a continued need in the clinic exists to prepare clinical grade MSC preparations with a predictable proliferation and immunosuppressive potential and minimal batch-to-batch variability. Therefore, the problem the present invention seeks to solve is to provide a process for the production/isolation of MSCs from bone marrow samples with improved characteristics.

The above problem is solved in a first aspect by a mesenchymal stromal cell (MSC) preparation, comprising MSCs isolated from bone marrow mononuclear cells (BM-MNC) characterized in that said MSC preparation is hTERT negative and polygenic. In preferred embodiments said MSC are mammalian, preferably human MSC.

The term "monogenic" when used in context to describe a sample or composition of cells refers to these cells originating from a common source or having the same genetic background. The term "polygenic" on the other hand refers to a composition of cells originating from different sources and having different genetic backgrounds. In context of the present invention a "polygenic MSC preparation" is a composition comprising MSCs having distinct genetic backgrounds, for example MSCs which originate from at least two genetically distinct bone marrow donors.

In the context of the herein described invention the terms "mesenchymal stromal cells" and "mesenchymal stem cells" shall be understood to be synonymous descriptions of the same multipotent cell fraction isolated from bone marrow samples.

In order to minimize the inter-donor variability as to their allosuppressive potential the inventors developed a unique three-step technique for the establishment of a GMP-compliant, serum-free MSC-Master Cell Bank from the pooled bone marrow mononuclear cells (BM-MNCs) of 8 third-party healthy donors: (i) isolation of mixed polygenic and cryopreservation of individual BM-MNCs from 8 third-party healthy donors in full agreement with the approval issued by the local Ethics Committee and Declaration of Helsinki, (ii) generation of MSCs from pooled BM-MNCs after thawing and cryopreservation in vials and (iii) thawing of MSC samples for their serum-free expansion and generation of "off-the-shelf" clinical-scale doses. In this manner, the inventors developed a surprisingly effective protocol for generation of clinical-grade MSC preparations with a constantly higher allosuppressive potential and constant proliferative capability, compared to MSCs generated from individual bone marrow donors. Therefore, this protocol provides clinical researchers with clinical-grade MSCs of a consistent quality for the treatment of graft-versus-host disease and other inflammatory disorders. Despite considerable up-front costs, this protocol ensures consistency, reproducibility, and reliability in immunosuppressive performance of clinical-grade MSCs.

Yet another embodiment pertains to a MSC preparation of the invention which is further characterized in that said MSCs are TERT negative. TERT is the telomerase reverse transcriptase (abbreviated to TERT, or hTERT in humans), which is a catalytic subunit of the enzyme telomerase, which, together with the telomerase RNA component (TERC), comprises the most important unit of the telomerase complex, necessary for maintaining proliferation capability of immortalized cells. The MSC preparation of the present invention is shown to comprise MSCs that are not immortal, which is in line with the absent hTERT expression.

One additional preferred embodiment of the invention is a MSC preparation as described herein, wherein said MSC preparation comprises
(a) At least 80%, preferably at least 95% CD73+ cells, most preferably at least 98%, and/or
(b) At least 80%, preferably at least 95% CD90+ cells, most preferably at least 98%, and/or
(c) At least 80%, preferably at least 95% CD105+ cells, most preferably at least 98%, and/or
(d) At least 80%, preferably at least 95% HLA-class I+ cells, most preferably at least 98%, and/or
(e) Less than 10%, preferably less than 1% CD45+ cells, most preferably less than 0.1%, and/or
(f) Less than 10%, preferably less than 1% CD14+ cells, most preferably less than 0.5%, and/or
(g) Less than 10%, preferably less than 1% CD34+ cells, most preferably less than 0.5%, and/or
(h) Less than 10%, preferably less than 5% HLA-DR+ cells, most preferably less than 1%.

In one additional embodiment the MSC preparation comprises
(a) At least 80%, preferably at least 95% CD73+ cells, most preferably at least 98%, and
(b) At least 80%, preferably at least 95% CD90+ cells, most preferably at least 98%, and
(c) At least 80%, preferably at least 95% CD105+ cells, most preferably at least 98%.

Additionally the MSC preparation of the invention may comprise
(e) Less than 10%, preferably less than 1% CD45+ cells, most preferably less than 0.1%, and
(f) Less than 10%, preferably less than 1% CD14+ cells, most preferably less than 0.5%, and
(g) Less than 10%, preferably less than 1% CD34+ cells, most preferably less than 0.5%.

The problem of the present invention is furthermore solved by an in-vitro method for the isolation of mesenchymal stromal cells, the method comprising: pooling bone marrow samples obtained from at least two genetically distinct donors to obtain a sample cell-pool, and thereafter isolating mesenchymal stromal cells from said sample cell-pool.

The process for the preparation or isolation of MSC from bone marrow samples in accordance with the present invention involves a step of pooling bone marrow, or a mononuclear cell fraction derived from bone marrow, from genetically distinct donors. Therefore, at least two genetically distinct bone marrow samples, or genetically distinct BM-MNCs fractions, are pooled in the method of the present invention. Importantly, the inventive method comprises the pooling of genetically distinct BM samples at a stage where the BM samples contain still a mixture of different cell types. Therefore, preferably the pooling of genetically distinct BM-MNC samples is done before the MSC fraction is purified or expanded from said samples. The pooling of the cells before the isolation of MSC yielded into MSC preparations with a surprisingly improved allo suppressive potential.

In one embodiment the method according to the invention comprises the steps of:
(a) Providing a number of bone marrow samples obtained from at least two genetically distinct donors,
(b) Pooling said bone marrow samples to obtain a sample cell-pool,
(c) Optionally, culturing said sample cell-pool, and
(d) Isolating from said sample cell-pool obtained in step (b) said mesenchymal stromal cells.

In one preferred embodiment the method comprises the steps of: Providing a number of bone marrow samples obtained from at least two genetically distinct donors, isolating the mononuclear cell fraction from bone marrow samples, pooling said bone marrow mononuclear cell samples to obtain a BM-MNC-pool, optionally, culturing said BM-MNC-pool, and isolating from said BM-MNC-pool said mesenchymal stromal cells. Of course all additional special variations of the inventive method as described herein above and below are equally preferable embodiments of this methodology which includes a step of isolating BM-MNCs from bone marrow samples.

The in vitro method for isolation of mesenchymal stromal cells (MSC) can further include the steps of a) determining the hTERT negative and polygenic status of the isolated mesenchymal stromal cells; and b) enriching the isolated mesenchymal stromal cells to obtain hTERT negative and polygenic isolated mesenchymal stromal cells.

The in vitro method for isolation of mesenchymal stromal cells (MSC) can further include the step of enriching the hTERT and polygenic isolated, enriched mesenchymal stromal cells to:
a) at least 95% CD73+ cells, and/or
b) at least 95% CD90+ cells, and/or
c) at least 95% CD105+ cells, and/or
d) at least 95% HLA-class 1+ cells, and/or
e) less than 1% CD45+ cells, and/or
f) less than 1% CD14+ cells, and/or
g) less than 1% CD34+ cells, and/or
h) less than 5% HLA-DR+ cells.

The term "sample cell-pool" in context of the invention shall refer to a mixture of bone marrow derived cells with different genetic background. Therefore, the sample cell-pool of the invention is polygenic. Most preferably a sample-cell pool in accordance with the invention is characterized in that MSCs are present only to a minor percentage of preferably less than 80%, preferably 70%, 60%, 50%, 40%, 30%, 20% and most preferably less than 10%, even more preferably less than 5%, less than 1%, most preferably less than 0.1%.

The term "genetically distinct" as used herein, indicates that at least one difference at the genomic level exists between bone marrow donors/subjects. Bone marrow can be collected from 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100 or more donors. Most preferred is the use of 4 to 8 different donor samples.

A "bone marrow sample" in accordance with the present invention may either be a bone marrow aspirate or from bone pieces, such as cancellous bone pieces. In a preferred embodiment a bone marrow sample is a bone marrow aspirate. How to collect a bone marrow sample is known to the skilled artisan. Said bone marrow samples of the invention in one preferred embodiment comprise a mixture of different cell types. For example each of said bone marrow samples comprises at least one non-adherent cell fraction and at least one adherent cell fraction. In one particular preferred embodiment said bone marrow sample is a bone marrow mononuclear cell (BM-MNC) sample or fraction. BM-MNCs are obtained from bone marrow.

In context of the present invention a "bone marrow mononuclear cell fraction" (also referred to herein as "BM-MNCs"), contains B, T and NK lymphocytes, early myeloid cells, and a very low number of endothelial progenitors, hematopoietic stem/progenitor and/or mesenchymal stromal cells.

In a preferred embodiment of the invention said bone marrow sample is a mammalian bone marrow sample and said mesenchymal stromal cell is a mammalian mesenchymal stromal cell. More preferred is that said bone marrow sample is a human bone marrow sample and said mesenchymal stromal cell is a human mesenchymal stromal cell.

Yet another embodiment of the invention pertains to the afore described process for the isolation of MSCs, the method further comprising a step (a') of extracting bone marrow mononuclear cells (BM-MNC) from each of said bone marrow samples to obtain BM-MNC-samples, and wherein in step (b), said BM-MNC-samples are pooled to obtain said sample cell-pool. As mentioned above, the BM-MNC fraction/sample contains only a small number of MSC. Therefore, in one preferred embodiment of the invention said BM-MNC samples to be pooled comprise a percentage of mesenchymal stromal cell per total cells in said sample of less than 80%, preferably 70%, 60%, 50%, 40%, 30%, 20% and most preferably less than 10%, even more preferably less than 5%, less than 1%, most preferably less than 0.1%.

In context of the herein described invention, in all of its embodiments and aspects, it is particularly preferred that said bone marrow samples (or BM-MNC samples) are obtained from at least three, more preferably at least four, more preferably at least five, more preferably at least six, more preferably at least seven, and most preferably at least eight genetically distinct donors. In other words, the MSC cell preparation and method for its production in one particularly preferred embodiment comprises the pooling of at least three, more preferably at least four, more preferably at least five, more preferably at least six, more preferably at least seven, and most preferably at least eight genetically distinct cellular samples.

Methods for the isolation of BM-MNCs from a bone marrow sample, in particular bone marrow aspirate, are well known to the person of skill. However, in one embodiment of the present invention it is preferred that BM-MNCs are isolated from a bone marrow sample using a cell density separation such as Ficoll gradient.

Once pooled, the obtained sample cell-pool of the invention is used to isolate and purify the MSCs. Methods for the isolation of MSCs from bone marrow samples or BM-MNCs are also well known in the art. A preferred method of the invention is the separation of adherent from non-adherent cells by simply removing floating cells by aspirating the cell culture medium from the culture container at regular intervals. By exchanging the medium multiple times the fraction of non-adherent cells is constantly reduced, whereas the adherent MSC-fraction continues to grow until confluency. These adherent cells are MSCs.

Thus, preferred is in one embodiment that step (d) of the method of the invention comprises a step of removing at least once the non-adherent cells from a culture of said sample cell-pool; or wherein after culturing said sample cell-pool, at least one detectable surface marker or antibody is used for the purification of said MSCs.

Additionally the method of the invention may provide a further step of either storing said isolated mesenchymal stromal cells, or expanding said isolated mesenchymal stromal cells.

In one additional aspect the invention includes a method for the production of clinical-grade MSC preparations. This method includes the aforementioned method steps for isolating MSCs, but furthermore includes the expansion of the isolated MSCs until receiving an amount of MSC applicable in the clinic. The expansion of the MSCs of the invention may either follow immediately after isolating the MSCs, or alternatively the isolated MSCs were stored via cryopreservation, by thawing an aliquot of cells for starting the expansion process. How MSCs are expanded is known in the art, and as an example explained in the example section of the present application.

Another aspect of the present invention pertains to a cellular composition comprising bone marrow samples from at least two genetically distinct bone marrow donors. Alternatively the cellular composition of the invention may comprise BM-MNCs from at least two genetically distinct bone marrow donors. Therefore, the cellular composition of the invention is preferably polygenic.

In one embodiment the cellular composition of the invention is obtainable by pooling at least two monogenic and genetically distinct bone marrow samples before isolating and/or expanding a stem cell fraction contained in said bone marrow samples. Thereby, via pooling, the cellular composition becomes polygenic.

In one preferred embodiment said bone marrow samples are bone marrow mononuclear cell samples.

One embodiment of this aspect pertains to a cellular composition of the invention, obtainable by a method comprising the steps
(a) Obtaining at least two bone marrow samples, each one of those from a genetically distinct bone marrow donor,
(b) Isolating from each of said bone marrow samples the bone marrow mononuclear cell fraction to obtain monogenic bone marrow mononuclear cell samples, and
(c) Pooling said monogenic bone marrow mononuclear cell samples obtained from each bone marrow sample to obtain the polygenic cellular composition.

It is understood that in context of the present invention a "bone marrow mononuclear cell fraction" comprises the standard cellular composition known for this cell fraction derived from bone marrow. In this regard it is preferred that said monogenic mononuclear cell samples are pooled before performing a further step of cellular purification or expansion, preferably before isolating or purifying any MSCs therefrom.

Yet another aspect of the invention provides a use of a mixture of bone marrow mononuclear cells obtained from at least two genetically distinct bone marrow donors in a method of isolating mesenchymal stromal cells.

Further provided is the aspect of a use of a cellular composition as described herein before in a method of purification/isolation of mesenchymal stromal cells.

The problem of the invention is also solved by a mesenchymal stromal cell obtainable by a method for isolating/purifying MSCs as described herein above.

The herein described MSC preparations or MSCs are preferably for use in medicine. MSCs are generally used in a wide variety of medical applications. Without intending to be restricted to the following examples, the MSCs of the invention are preferably for use in the treatment of autoimmune diseases such as multiple sclerosis, Type 1 diabetes, rheumatoid arthritis, uveitis, autoimmune thyroid disease, inflammatory bowel disease (IBD), scleroderma, Graves' Disease, lupus, Crohn's disease, autoimmune lymphoproliferative disease (ALPS), demyelinating disease, autoimmune encephalomyelitis, autoimmune gastritis (AIG), and autoimmune glomerular diseases. Particularly, the MSC preparation of the invention is used in the treatment of graft-versus-host disease (GVHD).

However, in context of the herein described invention, the MSC preparations are useful in any regenerative or autoimmune disease, preferably transient, relapsing or remitting. Other clinical applications of the inventive MSC preparations are in wound healing, corneal ulcer, stroke, or for facilitating of engraftment in allogeneic stem cell transplantation.

A cell therapy involving MSC administration is based, for example, on the following steps: harvest of MSC-containing tissue (bone marrow), isolate and expand MSCs in accordance with the herein described methods, and administer the MSCs to the subject/patient, with or without biochemical or genetic manipulation.

In one aspect, the invention provides a method of treating a subject in need thereof comprising the step of administering a therapeutic dose of an MSC preparation produced in accordance with the present invention.

A therapeutic dose for an autoimmune disease or graft-versus-host disease can contain about $1 \times 10^5$ cells/kg to about $1 \times 10^7$ cells/kg. In another embodiment, a therapeutic dose is about $1 \times 10^6$ cells/kg to about $5 \times 10^6$ cells/kg. In another embodiment, a therapeutic dose is about $2 \times 10^6$ cells/kg to about $8 \times 10^6$ cells/kg. In another embodiment, a therapeutic dose is about $2 \times 10^6$ cells/kg or about $2 \times 10^6 \pm$ about 10%, about 20%, or about 30% cells/kg. In another embodiment, a therapeutic dose is about $8 \times 10^6$ cells/kg or about $8 \times 10^6 \pm$ about 10%, about 20%, or about 30% cells/kg, and include any amounts or ranges there between. Given an MSC preparation of the present invention, the number of mesenchymal stromal cells to be administered is dependent upon a variety of factors, including the age, weight, and sex of the patient, the disease to be treated, and the extent and severity thereof.

The MSCs of the invention can be administered by a variety of procedures. MSCs can be administered systemically, such as by intravenous, intraarterial, or intraperitoneal administration. The mesenchymal stromal cells can be administered by direct injection to an organ or tissue in need thereof. The mesenchymal stromal cells can be applied topically. The mesenchymal stromal cells can be applied directly to a tissue in need thereof during a surgical procedure.

The mesenchymal stromal cells, in accordance with the present invention, can be employed in the treatment, alleviation, or prevention of any disease or disorder which can be alleviated, treated, or prevented through angiogenesis. Thus, for example, the mesenchymal stromal cells can be administered to an animal to treat blocked arteries, including those in the extremities, i.e., arms, legs, hands, and feet, as well as the neck or in various organs. For example, the mesenchymal stromal cells can be used to treat blocked arteries which supply the brain, thereby treating or preventing stroke. Also, the mesenchymal stromal cells can be used to treat blood vessels in embryonic and postnatal corneas and can be used to provide glomerular structuring. In another embodiment, the mesenchymal stromal cells can be employed in the treatment of wounds, both internal and external, as well as the treatment of dermal ulcers found in the feet, hands, legs or arms, including, but not limited to, dermal ulcers caused by diseases such as diabetes and sickle cell anemia.

Furthermore, because angiogenesis is involved in embryo implantation and placenta formation, the mesenchymal stromal cells can be employed to promote embryo implantation and prevent miscarriage.

In addition, the mesenchymal stromal cells can be administered to an unborn subject, including humans, to promote the development of the vasculature in the unborn subject.

In another embodiment, the mesenchymal stromal cells can be administered to a subject, born or unborn, in order to promote cartilage resorption and bone formation, as well as promote correct growth plate morphogenesis.

The mesenchymal stromal cells can be genetically engineered with one or more polynucleotides encoding a therapeutic agent. The polynucleotides can be delivered to the mesenchymal stromal cells via an appropriate expression vehicle. Expression vehicles which can be employed to genetically engineer the mesenchymal stromal cells include, but are not limited to, retroviral vectors, adenoviral vectors, and adeno-associated virus vectors. The MSCs of the invention can for example be genetically engineered to overexpress TERT, and thereby to immortalize the cells.

Also, the MSC preparation of the invention or the mesenchymal stromal cell can be for use in stem cell transplantation.

Further provided is a use of the MSC preparation or MSCs of the invention in the production of bone replacement material.

Another aspect of the invention is a method for the production of a medicament comprising mesenchymal stromal cells, comprising the method steps according to any of the herein described methods for the isolation/purification of MSCs.

In another embodiment, the MSCs of the present invention or produced with the methods of the invention can differentiate into osteoblasts, adipocytes and/or chondrocytes under appropriate culture conditions, such as the respective cell differentiation inducing conditions, for example cultured with the appropriate inducing medium, such as osteogenic, adipogenic and chondrogenic induction medium, respectively. In one embodiment, the appropriate culture conditions and appropriate inducing media are those specified in the Examples. In another embodiment, examples of suitable conditions and media are disclosed in Aubin J E. Osteoprogenitor cell frequency in rat bone marrow stromal populations: role for heterotypic cellcell interactions in osteoblast differentiation. J Cell Biochem. (1999) 72(3):396-410 (for osteogenesis); Falconi D, Oizumi K, Aubin J E. Leukemia inhibitory factor influences the fate choice of mesenchymal progenitor cells. Stem Cells. (2007) 25(2):305-312 (for adipogenesis); and Zhang S, Uchida S, Inoue T, Chan M, Mockler E, Aubin J E. Side population (SP) cells isolated from fetal rat calvaria are enriched for bone, cartilage, adipose tissue and neural progenitors. Bone. (2006) 38(5):662-670 (for chondrogenesis).

In one aspect of the invention, the invention provides a kit for conducting the method of the invention comprising one or more of the following: culture medium, and instructions for using same. In another embodiment the invention can provide a kit comprising a sample of isolated mesenchymal stromal cells of the present invention and optionally culture medium and or instructions for use in experiments and/or in transplantation.

The mesenchymal stromal cell (MSC) preparation as described herein is furthermore characterized in that it comprises MSCs isolated from bone marrow mononuclear cells (BM-MNC), that are polygenic, and having at least one of the following characteristics:
  (a) an increased p21 expression compared to the p21 expression in monogenic MSCs (generated from single donors),
  (b) a decreased p53 expression compared to the p53 expression in monogenic MSCs (generated from single donors), and/or
  (c) a decreased c-myc expression compared to the c-myc expression in monogenic MSCs (generated from single donors).

These characteristics might be used as alternative or additional structural features distinguishing the described MSC preparation of the invention from state of the art preparations. In one embodiment the MSC preparation of the invention comprises MSCs with an increased p21 expression compared to the p21 expression in monogenic MSCs (generated from single donors). The MSCs of the invention may further or alternatively characterized by a decreased p53 expression compared to the p53 expression in monogenic MSCs (generated from single donors).

The present invention in one embodiment relates to a MSC preparation, wherein said MSCs are further or alternatively characterized by a decreased c-myc expression compared to the c-myc expression in monogenic MSCs (generated from single donors).

In specific embodiments said increase in p21 expression is at least 2-fold, preferably at least 3 fold, more preferably at least 4 fold; and/or wherein said decrease in p53 expression is at least 10-fold, preferably at least 20 fold; and/or wherein said decrease in c-myc expression is at least 10-fold, preferably at least 20 fold, and most preferably not detectable.

Preferred MSC preparations of the invention comprise MSCs with all of the aforementioned characteristics (a) to (c). The isolated MSCs of the invention comprised at least one human MSC with a chromosomal translocation between chromosomes 5 and 9, which may be used as an additional characteristic of the MSCs of the invention. Preferably MSCs are characterized by (a) and (b), (a) and (c), or (b) and (c). Most preferably said MSCs are characterized by (a), (b) and (c). A MSC preparation is also preferred, wherein said difference in expression of p21, p53, c-myc, and/or hTERT is between invented MSCs and monogenic MSCs generated from single donors.

The present invention will now be further described in the following examples with reference to the accompanying figures and sequences, nevertheless, without being limited thereto. For the purposes of the present invention, all references as cited herein are incorporated by reference in their entireties. In the Figures:

FIG. 1: Collection of bone marrow and separation of bone marrow mononuclear cells. A) Bone marrow was collected from 8 healthy third-party donors in general anaesthesia by bilateral aspiration from the iliac crest. B) Bone marrow samples were collected in bags and anti-coagulated with 7-12% ACD-A and 7-12 i.U. of heparin per ml of marrow aspirate. C) Bone marrow mononuclear cells were enriched from bone marrow aspirate by Ficoll (GE Healthcare, Munich, Germany) density centrifugation using the Sepax II NeatCell process (Biosafe, Switzerland). D) BM-MNCs were washed twice and resuspended in the cryomedium consisting of 10% DMSO/5% HSA/X-vivo. E) Bags containing BM-MNCs from each bone marrow donor in cryomedium were frozen in the vapour phase of liquid nitrogen until use.

Figure 2:
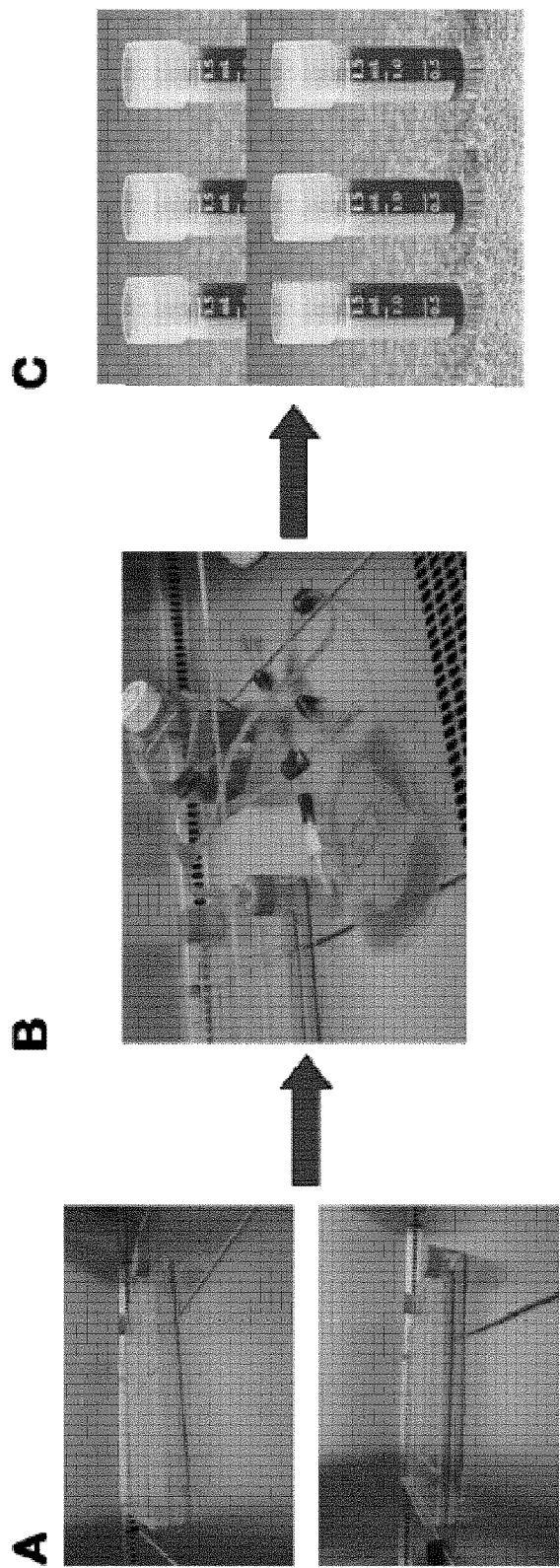

FIG. 2: Generation of the MSC-bank from bone marrow mononuclear cells. A) Bags containing bone marrow mononuclear cells of each donor were thawed at +37° C. and after washing twice with medium they were pooled in a definite volume of DMEM supplemented with 5% platelet lysate. All cells were plated in one 1-CellStack and eleven 2-CellStack plates B) After 72 hours the non-adherent fraction was removed and the adherent cells were further cultured in DMEM supplemented with 5% PL for another 11 days by changing medium every three days. Once the MSCs appeared and grew to a confluence of 80% MSCs were detached using trypsin (TrypLE) and after washing them with medium cell pellets were resuspended in cryomedium consisting of 10% DMSO/5% HSA/DMEM. C) MSCs were frozen in 210 cryovials, each containing $1.5 \times 10^6$ MSCs of passage P1. The inventors designated this set of vials with MSCs as a MSC-bank.

Figure 3:
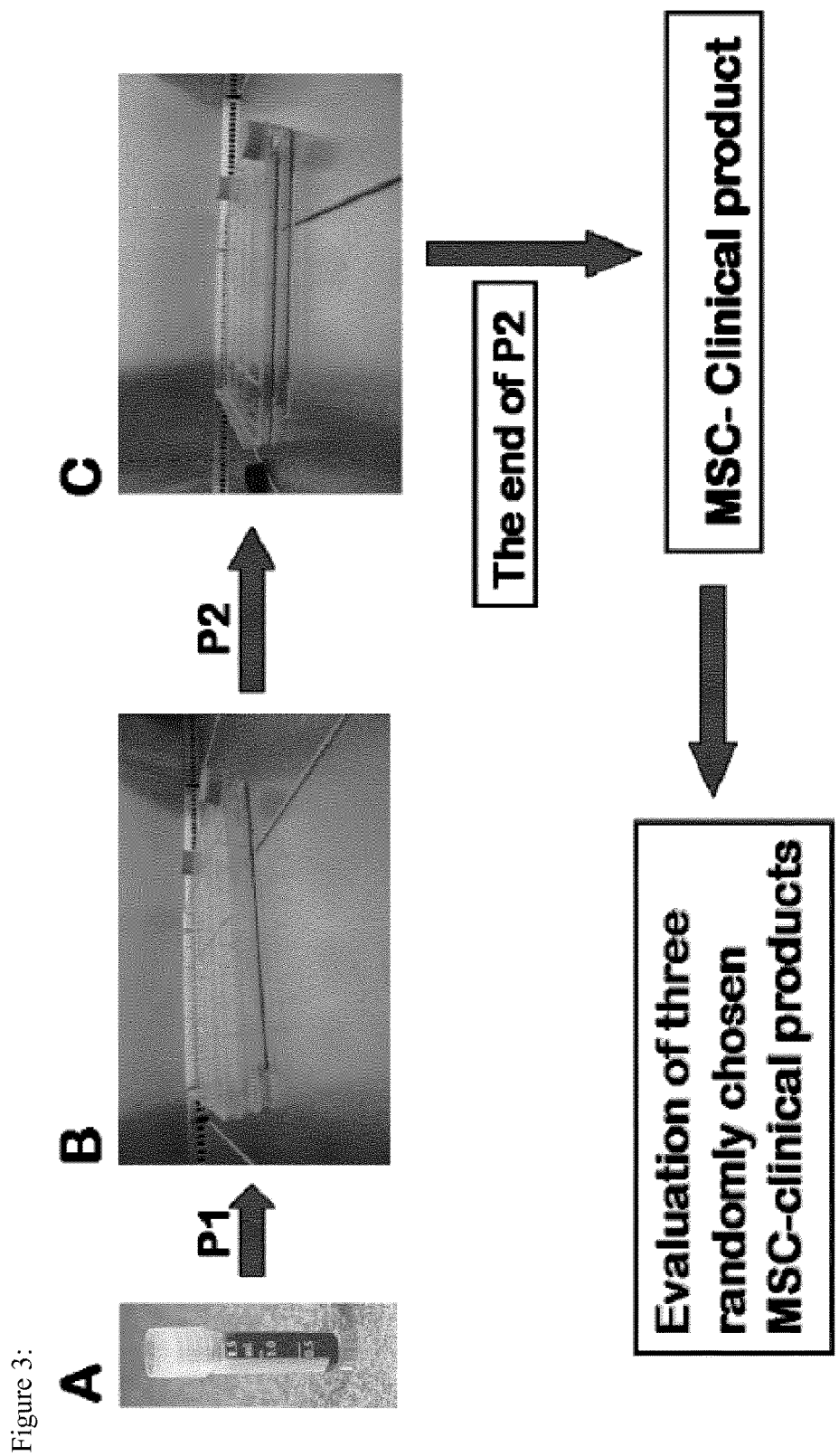

FIG. 3: Generation of MSC-clinical end products A) Three randomly-chosen cryopreserved vials with MSCs were thawed 6-8 weeks after their initial cryopreservation B) They were plated in one 1-CellStack (636 cm$^2$) and cultured for 6-7 days in DMEM containing 10% platelet lysate. The medium was changed every three days. C) On day 6 or 7 (according to their confluent growth) MSCs (the end of P1) were detached by trypsin, washed and plated in eight 2-Cell-Stacks at a cell concentration of $2 \times 10^3$ MSCs/1 cm2 and expanded for another week. Medium was changed every 3-4 days and at the end of the week (the end of P2) MSCs were detached by trypsin, washed twice and the cell number was counted. These MSCs were cryopreserved and designated as MSC clinical product, which after 2-3 weeks underwent validation concerning their proliferative, differentiation and allo suppressive potential.

Figure 4:
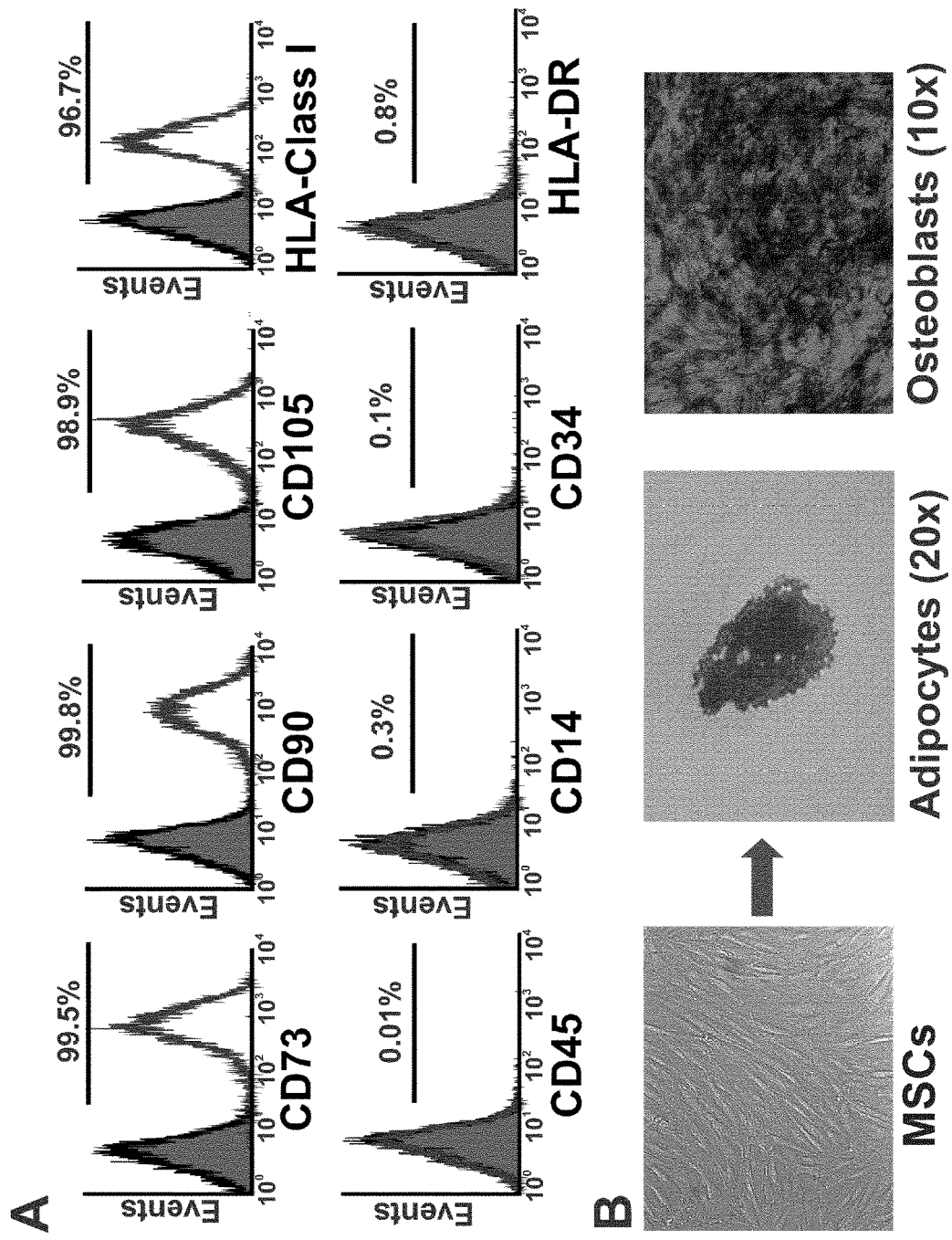

FIG. 4: Phenotype of MSCs and their differentiation potential. A) MSCs generated by expansion of the aliquots from MSC-bank at the end of passage 2 were labelled with mouse anti-human antibodies conjugated to fluorochromes as presented in the table 1. B) Culture of MSCs in the tissue-specific culture media induced their differentiation into adipocytes and osteoblasts.

Figure 5:
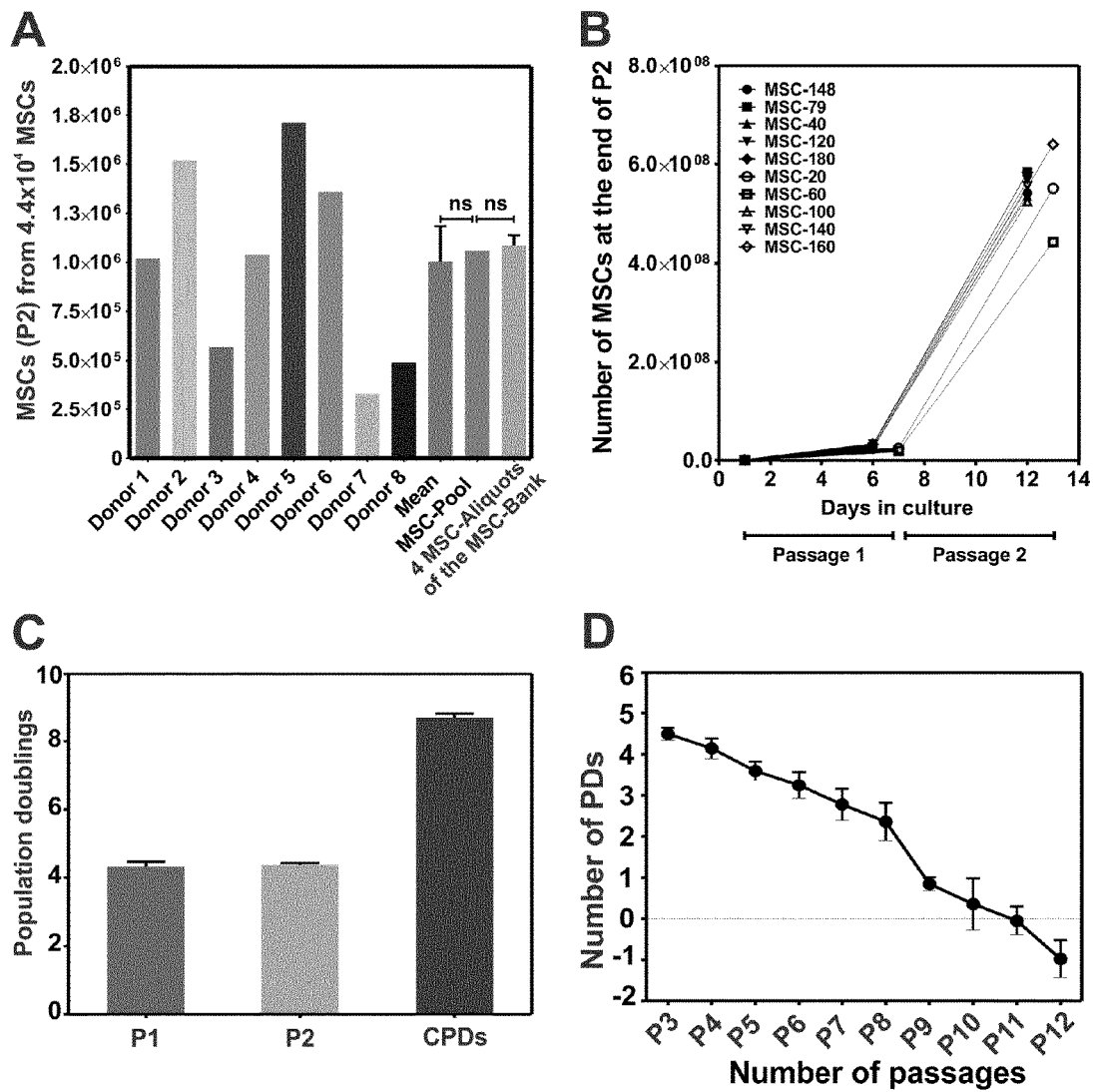

FIG. 5: Growth kinetics of MSCs from individual donors and the MSC-end products. A) The initial number of $4.4 \times 10^4$ MSCs from each bone marrow donor was expanded for one passage (from the start to the end of P2). At the same time, MSCs of all 8 donors were pooled and expanded from the start till the end of P2 (MSC-Pool) as well as 4 aliquots from the MSC-Bank. At the end of passage 2 the MSCs were trypsinized and their number was calculated; ns=not significant B) Ten MSC-cryovials of MSC-bank were thawed and expanded over two passages in order to assess their proliferation potential. Mean cell number of all expanded vials at the end of passage 2 was $5.3 \times 10^8 \pm 5 \times 10^7$ MSCs. C) MSCs showed approximately 4 population doublings (PDs) per passage, therefore the cumulative number of PDs (CPD) was $8.7 \pm 0.4$ PDs. D) To demonstrate that the MSC-end products are not immortal cells, the inventors assessed their growth kinetics for 12 passages and estimated the number of PDs. As it is shown in the figure from passage 9-12 these MSCs were not able to even duplicate themselves (n=3).

Figure 6:
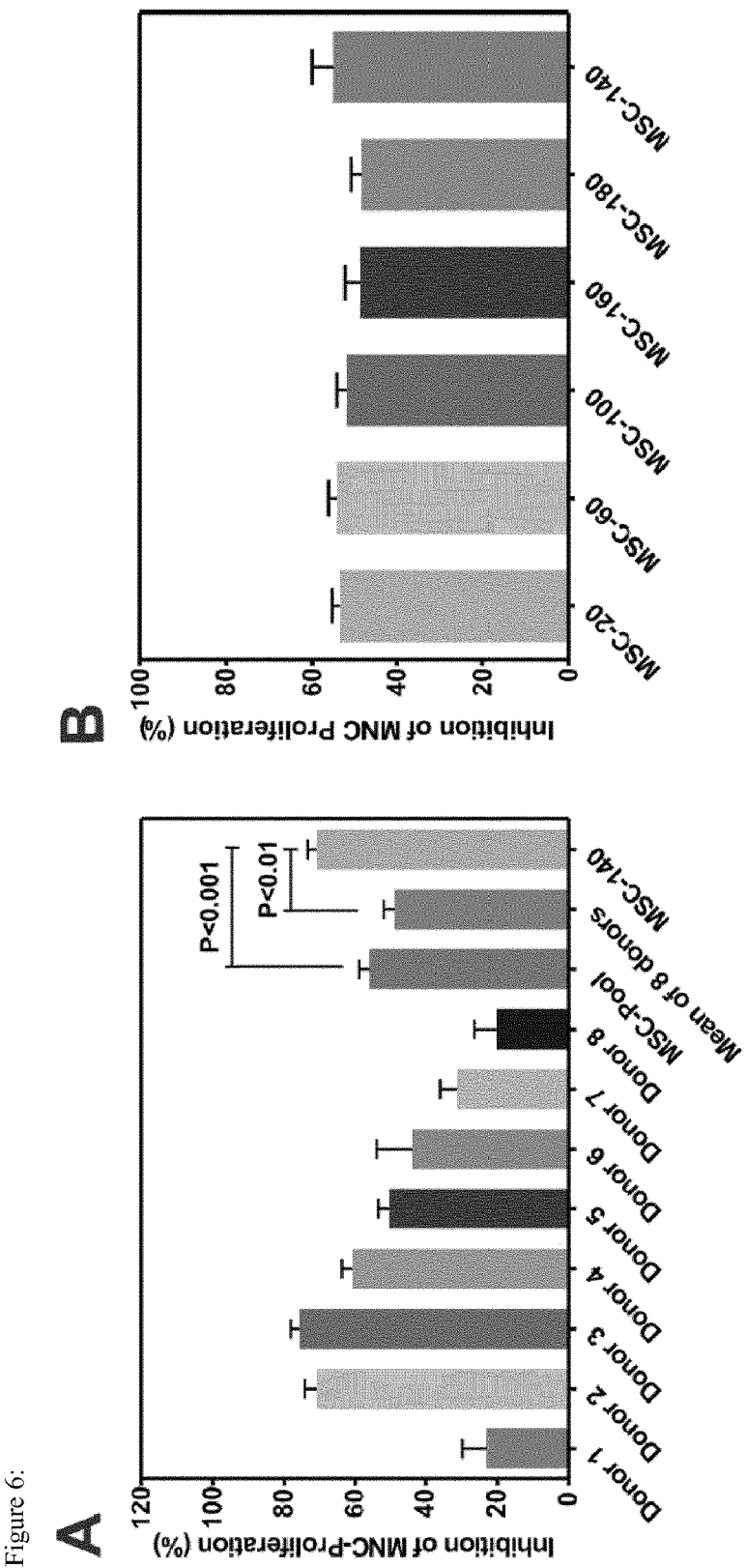

FIG. 6: Allosuppressive potential of MSCs generated from individual donors and MSC-end products. A) MSCs of passage 0 from 8 individual donors as well as the MSC-Pool that was generated by pooling the MSCs of 8 donors before expansion (MSC-Pool), and one MSC-end product (MSC-140) were expanded to the end of passage 2. Thereafter, the MSCs were trypsinized, washed twice in the medium and after determination of the cell counts and viability by trypan blue they were used to estimate their allosuppressive potential in MLR-assay. On day 6 BrdU was offered to the cells and next day the assay was performed in order to evaluate the inhibition of proliferation of allogeneic blood mononuclear cells from two HLA-disparate donors. B) Six MSC-end products (clinical doses) were thawed and after washing the cells they were directly used for the MLR-assay. The aim of these experiments was to find out whether thawed MSC-end products, as they are given to the patients, are able to suppress the allogen-induced proliferation of mononuclear cells from two allogeneic MNC donors.

Figure 7:
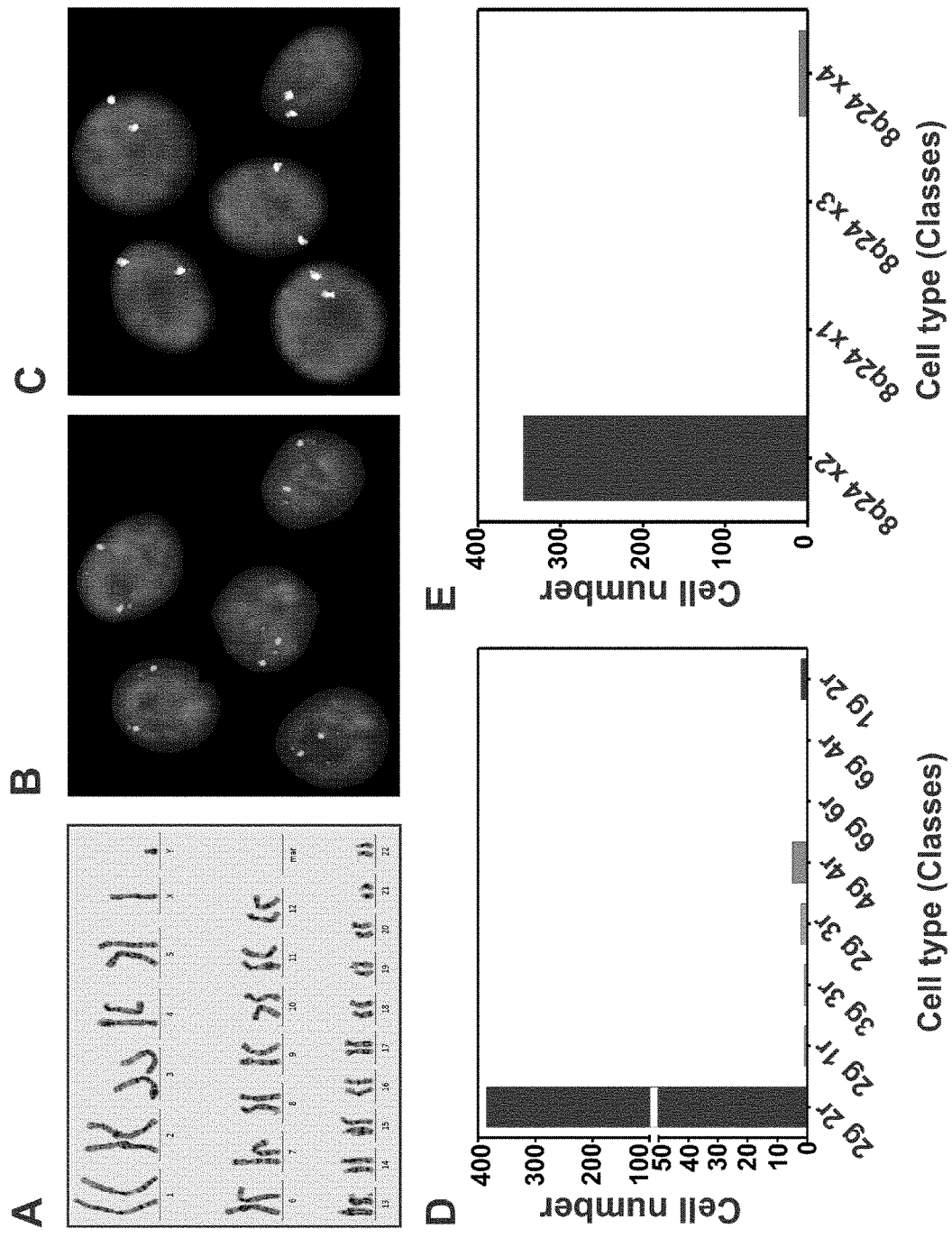

FIG. 7: Genetic characterization of the clinical-scale MSC-end product A) Normal karyogram of the clinical-grade MSC-end products at the end of passage 2. B) Interphase nuclei after two-color hybridization of probe set 5p15 (green) and 5q35 (red) identified a normal diploid pattern for the chromosome 5. C) Interphase nuclei after three-color hybridization of a MYC break apart probe showed in almost all cells two normal fusion signals. D) Number of MSCs with normal diploid and aneuploid pattern after two-color hybridization of probe set 5p15 and 5q35. Total number of analyzed MSCs was 396. E) Number of MSCs with normal diploid and aneuploid pattern after three-color hybridization of a MYC break apart probe for chromosome 8q24. Total number of analyzed MSCs was 356.

Figure 8:
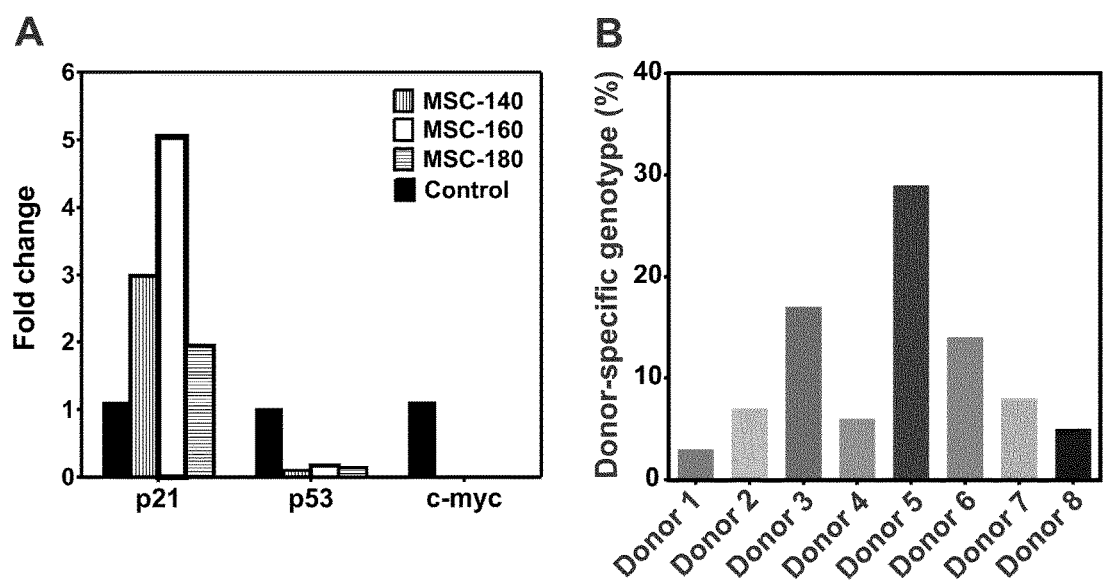

FIG. 8: Expression of transforming genes and chimeric analysis of the MSC-end products A) RT-PCR analysis of genes involved in the cell transformation in 3 clinical-scale MSC-end products. Total RNA was isolated from three MSC-end products and MSCs from one donor (control). After transcription into cDNA it was used to quantify expression of p21, p53 and c-myc by PCR. B) STR-PCR analysis of the clinical-scale MSC-end product. From the MSCs of the clinical-grade MSC-end product DNA was isolated, which then was used to evaluate specific STR-regions found on nuclear DNA. All eight donors' genotype was represented in the MSC-end product generated from pooled MNCs.

EXAMPLES

Materials and Methods
Raw Material Collection
Bone marrow was aspirated in general anaesthesia by bilateral aspiration from the iliac crest. Marrow was anticoagulated with 7-12% ACD-A and 7-12 i.U. of heparin per ml of marrow aspirate.

Infectious Disease Testing
The infectious disease marker panel exceeded minimal requirements of JACIE and the German Stem Cell Act. Thus as part of the donor work-up, evidence of seronegativity for HiV1/2, anti-HBc, HBsAg, anti-HCV, anti-HTLV1/2 (IgM and IgG for all), anti-Hepatitis A IgM, anti-Toxoplasma IgM, anti-EBV IgM, anti-CMV IgM and TPHA, as well as negativity by NAT for HiV, HAV, HBV, HCV and ParvoB 19 was sought; tests for HiV1/2, anti-HBc, HBsAg, anti-HCV, CMV, TPHA and the described NAT were repeated on the day of marrow donation. All donors met the criteria. Moreover, since CMV is a cell-resident virus, negativity for CMV genome in the bone marrow cell pellet was sought (Dept. of Virology, Goethe University, and Bioreliance, Glasgow, UK).

Processing Facility
All processes were performed under full GMP criteria in the clean room suite (class A in B) of the Department of Cellular Therapeutics/Cell Processing (GMP) which is part of the German Red Cross Blood Service and fully embedded into the quality management system thereof, with formal permission from the state government (manufacturing license acc. to § 20b/c (BM collection and testing) and § 13 (MSC generation and testing) German Medicines Act).

Bone Marrow Processing
Bone marrow mononuclear cells were enriched from bone marrow aspirate by Ficoll (GE Healthcare, Munich, Germany) density centrifugation using the Sepax II NeatCell process (Biosafe, Switzerland) as described by the manufacturer. All connections were established by sterile tube welding (TSCD, Terumo, Dusseldorf, Germany), so that an entirely closed process was used.

Collection of Platelet Concentrates and Generation of Platelet Lysates (PL)
As starting material for platelet lysates one to two day-old buffy coat pool platelets containing approximately 10% plasma in PASIII were used. Platelets were cleared for clinical use in accordance with German guidelines for blood products. Up to 4-6 platelet concentrates were pooled to generate one batch of platelet lysate. Platelets were aliquoted in an A in B environment into sterile 50 ml Falcon tubes and immediately frozen at −80° C. Individual aliquots were thawed after at least 24 h and centrifuged for 10 minutes at 3774×g with brake (acceleration 8, brake 4). The supernatants (platelet lysates) were collected and subjected to extended release testing, including freedom from bacteria (BacTAlert, Biomerieux) and potential to promote the adherence of progenitor cells for MSC and MSC-expansion.

Testing of Platelet Lysates
a) Potential of platelet lysates to promote the adherence of progenitor cells for MSCs Bone marrow mononuclear cells (BM-MNCs) were thawed at 37° C., washed twice with DMEM supplemented with 5% PL and after the last wash the cell pellet was resuspended in the DMEM supplemented with 5 UI Heparin/ml and 5% or 10% PL. BM-MNCs were plated at a density $1.71 \times 10e5/1$ cm2 and incubated for 72 hours at 37° C. with 5% $CO_2$ and saturated humidity. The non-adherent cell fraction was removed, while the adherent cells were further cultured for another 11 days. Culture medium was changed every 3-4 days. Once the spindle-shaped cells (MSCs) were confluent at 70-80% they were enzymatically detached by trypsin and their number was counted. This procedure was performed with both media i.e. DMEM supplemented with either 5% PL or 10% PL.

b) Capacity of PLs to Expand MSCs
The specification of platelet lysates was set as IDM-conforming to standards laid out in the German guidelines, freedom from bacteria, expansion of a cryopreserved aliquot of MSC by at least 2-fold within 7 days. Only platelets fulfilling these criteria were used for the generation of clinical MSC protocols.

Generation of MSC-Bank and Clinical-Grade End Products a) Generation of MSC-Bank Bags containing bone marrow mononuclear cells from each donor were thawed in Plasmatherm at +37° C. They were washed twice with DMEM supplemented with 5% PL by centrifugation for 10 minutes at 400 g and resuspended at a defined volume of DMEM+5% platelet lysate. After this step, cell suspensions from each donor were pooled together and the number of cells was counted by a cell counter (Sysmex). Thereafter, cell suspension pool was plated in eleven 2-CellSTACKs (per one 2-CellSTACK: 250×10e6 BM-MNCs/260 ml medium) and in 1 single CellSTACK (per 1-CellSTACK: 125×10e6 BM-MNCs/130 ml medium). After 72 h the nonadherent cells were removed using medium exchange bags (Macopharma, Langen, Germany) and adherent cells were cultured further for another 11 days with DMEM supplemented with 5% PL until the MSCs were 80-90% confluent. In this period the medium was changed every 3-4 days. On day 14 before detachment of the MSCs, from each CellSTACK was taken 5 ml of culture medium which was pooled in a sterile bottle to be tested for sterility for aerobic and anaerobic bacteria and fungi. Thereafter, the cells were detached using synthetic TrypLE (Life Technologies, Darmstadt, Germany) and after washing them with DMEM+5% PL, the cells were centrifuged for 7 minutes at 400×g. Cell pellets were resuspended in defined volume of medium and the cells were counted with trypan blue in a hemacytometer. The inventors obtained in total 320×10e6 passage 1 MSCs. Two-million cells were used for determination of the phenotype by means of flow cytometry. The rest of MSCs was centrifuged for 7 minutes at 400×g.

The cells were resuspended in 5% HSA/DMEM whereby the number of MSCs was adjusted to 3×10e6 cells/ml. One volume of cell suspension was slowly mixed with one volume of cold freezing medium containing 20% DMSO/ 5% HSA/DMEM. Therefore, the final concentration of MSCs was 1.5×10e6/ml cell suspension, whereas the final concentration of cryomedium was 10% DMSO/5% HSA/DMEM. The cells were distributed in 210 cryovials (each 1.5×10e6 MSCs of passage 1) and then cryopreserved by using a Cryoserve controlled-rate freezer (Schollkrippen, Germany) according to established protocols. The frozen vials were stored in vapour phase of liquid nitrogen (Tec-Lab, Idstein, Germany). In addition, the rest of MSCs was mixed with freezing medium and tested for sterility (aerobic and anaerobic bacteria and fungi).

b) Generation of Clinical-Scale MSC-End Products

To generate and validate the clinical-scale MSC-end products, MSC-bank vials were successively thawed per random 6-8 weeks after their cryopreservation. After thawing at 37° C. MSCs were washed in culture medium containing 10% PL, whereby the cell count viability was assessed using trypan blue staining in hemocytometer. The cells of one MSC-bank vial was plated in one 1-CellStack (636 cm$^2$) and cultured with DMEM supplemented with heparin (5 IU/ml medium) and PL 10% (V/V). The medium was changed on day 4 and on day 6-7 the cells were detached using TrypLe and then further plated in eight 2-CellStacks (each 1,272 cm$^2$) as passage two at a density 2×10$^3$ cells/cm$^2$. The procedure was repeated as for passage 1 and on day 6-7 the MSCs were harvested. After washing with 0.5% HSA/0.9% NaCl, viable MSCs were counted by trypan blue staining. Further, clinical-scale MSCs were resuspended in cryomedium (0.9% NaCl with 5% HSA and 10% DMSO) as end passage 2 MSCs and distributed in 4-7 cryobags containing each 4.2 to 5.5×10e7 MSCs in a volume of 45 ml freezing medium. Samples were cryopreserved using a Cryoserve controlled-rate freezer (Schollkrippen, Germany) using established protocols and stored in vapour phase of liquid nitrogen (Tec-Lab, Idstein, Germany).

Quality Control Tests

All tests were performed with thawed MSC-end products without expansion, in a state in that they are administered to the patients for clinical application.

a) Cell Enumeration and Viability of Thawed MSCs

Total cell enumeration was done using a Neubauer chamber hemacytometer. MSC viability was assessed using trypan blue staining.

b) Phenotypic Characterization

Flow cytometric analysis was performed using the ISCT minimal criteria for MSCs. To determine the phenotype of thawed MSCs the inventors stained them with following fluoro-chrome-conjugated mouse anti-human monoclonal antibodies as presented in table 1.

TABLE 1

Antibodies used for determination of the phenotype of MSCs

| Antibodies | Company | Cat. Nr. | Clone | Isotype |
|---|---|---|---|---|
| IgG1 FITC | BioLegend | 400109 | MOPC-21 | IgG1 |
| IgG2a FITC | BioLegend | 400209 | MOPC-173 | IgG2a |
| IgG1 PE | BioLegend | 400113 | MOPC-21 | IgG1 |
| IgG1 PerCP | BioLegend | 400147 | MOPC-21 | IgG1 |
| CD45 FITC | BioLegend | 304005 | HI30 | IgG1 |
| CD34 FITC | BioLegend | 343603 | 561 | IgG2a |
| CD14 FITC | BioLegend | 325603 | HCD14 | IgG1 |
| HLA-DR FITC | BioLegend | 307603 | L243 | IgG2a |
| CD90 FITC | BioLegend | 328107 | 5E10 | IgG1 |
| CD73 PE | BioLegend | 344003 | V B-CD73.3 | IaG1 |
| CD105 PE | BioLegend | 323205 | 43A3 | IgG1 |
| Propidium iodide (PI) Solution | BD Pharmingen | 556463 | | | d) Evaluation of the Allosuppressive Potential of MSC-End Products

To test the immunosuppressive effect of the MSC-end products on the alloantigen-driven reaction, the inventors used mixed lymphocyte reaction (MLR). Peripheral blood mononuclear cells (PB-MNCs) from healthy unrelated donors were isolated using a Ficoll-gradient (density 1.077, Biochrom KG, Berlin, Germany), washed twice with PBS and resuspended in RPMI-1640 with 10% FBS (Invitrogen). PB-MNCs of 2 unrelated donors were cultured in black 96-well plates for six days either alone (control group) or mixed with third-party, lethally irradiated (30 Gy) MSC-end products at an MSC:PB-MNC ratio of 1:1 (1×10$^5$ MSC:1× 10$^5$ PB-MNC). The inventors assessed six MSC-end products directly after thawing as well as MSCs of all eight donors, whose BM-MNCs were pooled and served as a source for generation of the inventor's master MSC-bank. All MLRs were performed in triplicates in a 96-well plate. On day 6, cells were incubated with 5-bromo-2'-deoxyuridine (BrdU) (Roche Diagnostics GmbH, Mannheim, Germany) for 24 h. The following day, relative light units (RLU/s) were measured with a luminometer 1420 Multilabel Counter Victor 3 (Perkin Elmer, Rodgau-Jügesheim, Germany). Proliferation levels of PB-MNCs were determined on day 7 using a BrdU assay. The inhibitory effect of MSC-end products on the proliferation of allogeneic MNCs was calculated as a percentage using the following formula:

100−[(proliferation of allogeneic PB-MNCs in presence of MSC/proliferation of PB-MNCs without MSCs)×100].

e) Determination of the Senescence of MSC-End Products In Vitro

To demonstrate that the MSC-end products are not immortal cells, the inventors assessed their growth kinetics over 12 passages. For each passage the medium was changed every 3 to 4 days and detachment of MSCs by TrypLE was performed according to their proliferation potential. To more precisely estimate their growth kinetics the inventors calculated the number of population doublings (PDs) by using the following formula:

PD for each subculture: [log 10(NH)−log 10(NI)/] log 10(2);

where NH=cell harvest number, NI=inoculum number of cells.

f) Differentiation Potential of MSC-End Products

To study differentiation potential along adipogenesis and osteogenesis MSC-end products of passage 2 were thawed and directly cultured in the appropriate tissue-specific induction media according to manufacturer's instructions (Miltenyi Biotec GmbH).

Adipogenesis

In order to generate adipocytes, the number of thawed MSCs was adjusted to 5×10e4 cells/1 ml of NH AdipoDiff Medium. Then, 1.5 ml of such a cell suspension were cultured in 35 mm cell culture dishes at 37° C. in an incubator with 5% CO2 and >95% humidity. The medium was changed every 3 d day and after 2-3 weeks large vacuoles started to appear. On day 30 the adipocytes were rounded and filled with lipid droplets, which the inventors stained with Oil Red O (Millipore, Schwalbach, Germany), a lipophilic red dye.

Osteogenesis

Briefly, concentration of thawed MSCs was adjusted to 3×10e4 cells/1 ml of NH OsteoDiff Medium. Then, 1.5 ml of such a cell suspension were cultured in 35 mm cell culture dishes at 37° C. in an incubator with 5% CO2 and >95% humidity. The medium was changed every 3 d day. On day 10 the osteoblasts can be identified morphologically by their cuboidal appearance and by their association with newly synthesized bone matrix. These cells are visualized by alkaline phosphatase staining (Sigma, Deisenho fen, Germany), since committed osteogenic cells express high levels of this enzyme. As a result of this staining the osteoblasts appear as dark purple stained cells. Tissue-specific stainings were evaluated using an Olympus IX71 microscope equipped with Soft Imaging System F-View II camera and cellSens Dimension imaging software.

g) Genetic Analysis of the Clinical-Grade MSC-End Products

RT-PCR analysis of the expression of transforming genes of clinical-scale MSC-end products. RNA was extracted using the RNeasy mini kit (Qiagen) followed by reverse transcription with 1 µg of total RNA using the Verso cDNA Kit (Thermo Scientific) with random hexanucleotides according to manufacturer's instructions, respectively. For the c-myc. p21, p53 and GAPDH gene real time PCR was performed on an Eppendorf realplex using the Quanti Tect SYBRE green qPCR master Mix (Qiagen). Detection of hTERT and ABL gene transcription was performed on a Biorad MyiQ Cycler using the Absolute qPCR ROX mix (Thermo Scientific). Oligonucleotides were purchased at Eurofins MWG. Primer sequences and PCR conditions except the reaction mix specific activation periods have been published in detail elsewhere.

h) Interphase Fluorescence In Situ Hybridization (FISH)

Interphase FISH analysis was performed according to the manufactures's protocols using following probes for chromosome 5 and 8: a two-color probe for chromosome 5p15 (hTERT) and 5q35 (NSD1, Kreatech, Amsterdam, NL) as well as a three-color break apart probe for the chromosome 8q24 (MYC, Kreatech, Amsterdam, NL). Evaluation of the hybridization signals was done on an automatic spot counting system (Applied Spectral Imaging, Edingen/Neckarhausen, Germany). For each probe >300 nuclei were scanned and classified using a threshold of 5%.

Documentation

Prior to generation of the MSC-cell bank, the clinical specimen for testing and the clinical specimen for release, the process had been formally validated in small-scale cultures, based on which manufacturing instructions (SOPs), batch records, testing instructions and protocols, as well as specifications were formally defined. A manufacturing license for a MSC-cell bank as well as for clinical specimen for use in clinical trials was obtained from the state government. Quality specifications were set after formal advisories obtained from the Federal drug agency, the Paul Ehrlich Institute.

Statistical Analysis

Statistical significance was analyzed using GraphPad Prism 5 software (GraphPad Software, San Diego, Calif., USA). Significance was assessed using the Student's t test. A P value less than 0.05 was considered statistically significant.

Example 1

Collection of Bone Marrow from 8 Healthy Third-Party Donors and Isolation of BM-MNCs After obtaining a written informed consent, from each bone marrow donor were collected up to 250 ml additional bone marrow aspirate for the purpose of MSC banking with approval by the local Ethics Committee in full agreement with the Declaration of Helsinki. In total from 8 donors the inventors obtained 1.66 liters bone marrow. For isolation of bone marrow mononuclear cells by Ficoll-gradient the inventors used the Sepax machine as shown in FIG. 1. The absolute number of BM-MNCs per 1 ml of bone marrow after this isolation procedure was $3.3 \times 10^6 \pm 6.3 \times 10^5$ cells. Total number of BM-MNCs which was obtained from eight donors after two washing steps was $9.86 \times 10^9$. These cells were resuspended in cryomedium and distributed in the bags, that were frozen using a rate-controlled freezer and then stored in the vapour phase of liquid nitrogen until use.

Example 2

Generation of Mesenchymal Stromal Cells from Bone Marrow Mononuclear Cells-Establishment of the MSC-Bank To generate the MSC-Bank, bone marrow mononuclear cells from 8 donors were thawed, washed and pooled in DMEM supplemented with 5% PL. To find out the optimal concentration of platelet lysate for the adherence of progenitor cells of MSCs the inventors cultured BM-MNCs with both concentrations of PL: 5% and 10%. The obtained results have demonstrated that the 5% concentration of platelet lysate is much more efficacious in promotion of BM-MNCs and generation of MSCs than 10% concentration of PL (FIG. 2A). In addition, the inventors asked which of these two concentrations of PLs is better for clinical-scale expansion of MSCs. The inventors found that that the 10% concentration of PLs is significantly more efficient in expanding the MSCs than the 5% PL (FIG. 2B). Moreover, in both cases the unfiltered platelet lysates were more effective for generation and expansion of MSCs than the filtered ones (FIG. 2C). These preliminary experiments paved the way for establishing the master MSC-bank. Therefore, the inventors thawed the BM-MNCs from each donor and after washing twice they were pooled together and thereafter cultured for 14 days, as described in the section of methods. The inventors were able to generate from $9.89 \times 10^9$ BM-MNCs $3.2 \times 10^8$ MSCs of passage 1. These MSCs expressed the typical markers for MSCs, such as CD73, CD90 and CD105 but were negative for hematopoietic cell markers e.g. CD14, CD34, CD45. They did not express HLA-Class II antigens but expressed high levels of HLA-Class I antigens. According to trypan blue staining the viability of these MSCs before freezing was 95±5%.

The total number of MSCs was distributed in 210 cryovials each containing 1.5×10e6 MSC P1 and finally frozen in the gaseous phase of liquid nitrogen until use. The inventors referred to this set of vials as MSC-bank.

Example 3

Generation and Validation of the Clinical-Scale MSC-End Products a) Thawing of Vials from MSC-Bank To generate and test clinical-scale MSC-end products concerning their proliferative, differentiation and allosuppressive potential, the inventors thawed three randomly chosen MSC-vials from the inventor's bank 6-8 weeks after their cryopreservation. The cell mean average recovery from three thawed vials was $1.39 \times 10^6$ viable cells/vial (range $1.23 \times 10^6$ to $1.48 \times 10^6$), whereas the viability was 95, 25% (range 93, 45%-96.9%). In average, expansion of these MSCs over 2 weeks until the end of passage 2 resulted in generation of $470 \times 10^6$ viable MSCs (range $420-548 \times 10^6$ MSCs). These samples were frozen in bags until use and referred to as clinical-scale MSC-end products.

b) Immunophenotyping of MSC-End Product and Their Differentiation Potential

MSCs of the clinical end product at the end of passage 2 were negative for the hematopoietic markers CD45, CD14, CD34 and did not express HLA-DR. However, they expressed high levels of the typical MSC-markers like CD73, CD90 and CD105. They were also able to differentiate along osteoblasts and adipocytes in the tissue-specific media (FIG. 4).

d) Proliferation Kinetics and Senescence of MSCs

To demonstrate the rationale of pooling the bone marrow mononuclear cells from 8 donors in order to establish the inventor's MSC-bank, the inventors compared in vitro growth of MSCs from 8 individual donors with the growth of pooled MSCs from each donor within P2 and 4 MSC-end products within the same passage (FIG. 5A). As expected, the MSCs of each bone marrow donor showed different growth kinetics varying from $0.3 \times 10^6$ (donor 7) to $1.7 \times 10^6$ MSCs (donor 5). The mean proliferation kinetics of the MSC-product generated from pooled BM-MNCs of 8 donors was $1.0 \times 10^6 \pm 0.5 \times 10^6$ MSCs, which correlated astonishingly good with the number of MSCs generated from the pool of individual MSCs of 8 donors: $1.1 \times 10^6$. More interestingly, both values correlated very well with the mean number of MSCs obtained from the expansion of 4 MSC-end products within a passage: $1.085 \times 10^6 \pm 0.1 \times 10^6$ MSCs. These results, proved the inventor's assumption that by pooling the BM-MNCs it is possible to generate an "arithmetical mean" of good and poorly proliferating MSCs.

In order to test the expectation that each MSC-end product from the MSC-bank possesses nearly the same proliferation potential the inventors analyzed it in expanded ten aliquots of the MSC-bank from P0 to the end of passage 2 for clinical application. As shown in FIG. 5B the mean cell number of all expanded end products at the end of passage 2 was $5.3 \times 10^8 \pm 5 \times 10^7$ MSCs, indicating a highly homogeneous proliferation potential of the end products. Likewise, the number of population doublings in P1 and at the end of passage 2 was rather the same (4.3 PDs/passage) and cumulative number of PDs did not exceed the value 9 (8.7±0.4). To test that MSCs are not immortal the inventors expanded 3 MSC-end products from the inventor's MSC-bank over 12 passages. As shown in FIG. 5D, from passage 5 to 12 the MSCs undergo replicative senescence and the number of PDs was promptly diminishing, indicating that these cells are indeed senescent and do not proliferate indefinitely.

e) Allosuppressive Potential of MSCs Isolated from Individual Donors and MSC-End Products in Mixed Lymphocyte Reaction (MLR)

MSCs have been shown to exert allosuppressive properties either in vitro or in vivo. To test the inventor's assumption that MSCs generated from the pool of BM-MNCs of 8 donors may have a higher allosuppressive potential than the average allosuppressive potential of MSCs generated from individual donors, the inventors used in MLR the expanded MSCs of passage 2 from 8 individual donors as well as the MSC-pool that was generated by pooling the MSCs of 8 donors before expansion (MSC-Pool), and one MSC-end product (generated from the MNC-pool derived MSC-bank: MSC-140). As expected, the allosuppressive potential of indiidual MSCs was very heterogeneous, i.e. these MSCs inhibited quite differently the alloantigen-induced proliferation of blood MNCs from two HLA-disparate donors. This effect ranged from 20% (donors 1 and 8) to about 80% inhibition (donors 2 and 3) (FIG. 6A). The allosuppressive potential of MSC generated from the pool of MSCs from 8 donors (MSC-Pool) was equal to the mean inhibitory potential of MSCs from 8 donors together (mean of 8 donors). However, the allosuppressive potential of the expanded MSC-140 sample from the inventor's MSC-bank was significantly higher than that of MSC-Pool and the mean allosuppressive potential of MSCs from 8 donors together (P<0.001, P<0.01, respectively). In order to assess whether the inventor's MSC-clinical products after thawing are homogeneous in suppressing the alloreaction, the inventors thawed 6 back-up vials with MSCs and directly tested in MLR assay, as they are administred to patients in vivo. As shown in the FIG. 6B all these 6 clinical MSC-products demonstrated a constant allosuppressive effect in vitro, indicating their very homogeneous potential in suppressing the alloreaction. The mean allosuppressive potential at the target-effector ratios used here was 52%±8.7%.

Example 4

Genetic Characterization of the Clinical-Grade MSC-End Products

As in vitro culture may usually be the source of chromosomal aberrations of cultured cells, the inventors asked whether the inventor's clinical-grade MSC-end products are subject to such changes. Chromosomal analysis of 25 MSCmitoses with a resolution of approximately 350-400 bands demonstrated a normal number of chromosomes (euploidy) in all of them (FIG. 7A). However, by using a resolution of approximately 300 bands the inventors found a translocation between the short arm of chromosome 5 and the short arm of chromosome 9 in 4 out of 25 analyzed mitosis. The breakdown points were localized in the band 5p13 and 19p13.3. Fluorescent in situ hybridization (FISH) analysis using a two-color probe for chromosome 5p15 (hTERT) and 5q35 (NSD1) as well as a three-color break apart probe for the chromosome 8q24 demonstrated that the majority of clinical-grade MSC-end products from the inventor's MSC-bank possess a normal diploid pattern for both chromosomes (FIG. 7B, C). Interphase nuclei after two-color hybridization of probe set 5p15 (green) and 5q35 (red) identified that 97.2% of cells demonstrated a normal diploid pattern for chromosome 5 and only about 2.8% showed a tetraploid hybridization pattern (FIG. 7D). Likewise, interphase nuclei after three-color hybridization of MYC break apart probe (FIG. 7C) showed in 97% of MSCs two normal fusion signals for chromosome 8q24 and 3% of MSCs with a tetraploid signal pattern (FIG. 7E). Thus, a very small fraction of MSCs acquire chromosomal aberrations in vitro.

Analysis of p53, p21 and Myc gene expression in 3 clinical-scale MSC-end products demonstrated a 2 to 5-fold increase in expression of p21, an about 6 to 10-fold reduction of p53 gene expression and no expression of the proto-oncogene c-myc (FIG. 8A). Most importantly, in consent with the senescent behaviour of MSCs from the inventor's bank, the inventors demonstrated that none of the 3 MSC-end products expressed hTERT (data not shown).

As the MSCs of the inventor's bank were generated from the pool of BM-MNCs of 8 third-party donors, the inventors were interested in the relative contribution of each donor after generation of the MSCs. Chimeric analysis by STR-PCR using a series of genetic markers demonstrated the presence of 8 donors in different proportions within the clinical-scale MSC-end product (FIG. 8B). In principle, the percentage of presence in the clinical product correlated with the proliferation potential of MSCs generated from individual donors i.e. MSCs that individually expanded better were also found in higher proportions in the MSC-end product.

Example 5

Clinical Cases of Patients Treated with MSC Preparations of the Invention

Patient 1 born Mar. 26, 1999
Disorder: Thalassemia major
After receiving stem cell transplantation the patient developed ascites, a swelling of the joints, pericardial effusion, caused by an immunological polyserositis, possibly in the context of graft versus host disease (GvHD). The administration of MSC of the invention once proceeded without complications. Under concomitant treatment with a diuretic the ascites, the swelling of the joints and pericardial effusion disappeared.

Patient 2 born Dec. 20, 2009
Disorder: severe agranulocytosis
On day +12 after stem cell therapy (SCT), the patient showed an acute foudroyante GvHD of the skin (grade IV), which even with 2 mg/kg steroid and 55 mg/kg Mofetilmycophenolat daily was uncontrollable. On Nov. 22, 2012 the child received the inventive MSC.

After MSC therapy the GvHD slowly but constantly declined, until it could no longer be detected after day 28 of MSC administration. The child has tolerated the MSCs very well and showed no viral, bacterial or fungal infection in the 30 days after administration.

Patient 3 born Mar. 25, 2010
Disorder: acute hymphoblastic leukemia;
SCT was on 16 Oct. 2012 from an HLA-non-identical, related, donor. Already on day +14 after SCT, the first signs of GvHD in the intestine were noted. Immediate therapy with Mofetilmycophenolat and steroid was started. That led to a relative improvement in symptoms. On day +35 after SCT, however, an intestinal GvHD grade II remained in spite of long-term steroid administration.

The decision was therefore taken to consolidate the immunosuppressive therapy by the administration of the inventive MSCs. The MSC administration took place without complications on Dec. 21, 2012. No infections showed up in the 30 days after SCT administration. On 15 Jan. 2013 no signs of intestinal GvHD in the patient could be observed, and only a mild GvHD of the skin that did not require any treatment remained.

Patient 4 born Mar. 25, 1999
Disorder: acute myeloid leukemia;
SCT on Dec. 19, 2012 from an HLA—Non-Identical, Related Donor 5 months after stem cell transplantation, the patient developed clinical symptoms of Stevens-Johnson syndrome. Since the patient at the time of recording took several medications that are associated with the development of this clinical picture, the respective medication was ended (voriconazole, penicillin, co-trimoxazole). Due to the detection of an adenovirus infection, it was decided not to conduct a immunosuppressive therapy with glucocorticoids. The patient developed also typical GvHD skin lesions that were probably stimulated by the Stevens-Johnson syndrome. Therefore, the immunosuppressive therapy with CSA was initiated. In order to dampen the inflammatory events, MSCs of the invention were administered. This MSC administration was well tolerated. Also a glucocorticoid-containing cream was administered several times a day. Under this therapy, there was an almost complete healing of the GvHD skin lesions.

The invention claimed is:

1. An in vitro method for the isolation of mesenchymal stromal cells (MSC), comprising the steps of:
   a) pooling individual bone marrow samples obtained from at least two genetically distinct donors to obtain a sample cell-pool; and
   b) isolating mesenchymal stromal cells from said sample cell-pool.

2. The method according to claim 1, further including the step:
   culturing said sample cell-pool prior to isolating mesenchymal stromal cells from said sample cell-pool.

3. The method of claim 1, wherein said bone marrow sample is a mammalian bone marrow sample and said mesenchymal stromal cell is a mammalian mesenchymal stromal cell.

4. The method according to claim 1, wherein said bone marrow samples are bone marrow mononuclear cell samples.

5. The method according to claim 1, wherein said bone marrow samples are obtained from at least three, at least four, at least five, at least six, at least seven, or at least eight genetically distinct donors.

6. The method according to claim 1, further including the step of storing said isolated mesenchymal stromal cells.

7. The method of claim 1, further including the steps of:
a) determining the hTERT negative and polygenic status of the isolated mesenchymal stromal cells; and
b) enriching the isolated mesenchymal stromal cells to obtain hTERT negative and polygenic isolated mesenchymal stromal cells.

8. The method of claim 7, further including the step of enriching the hTERT negative and polygenic isolated, enriched mesenchymal stromal cells to:
a) at least 95% CD73+ cells,
and/or
b) at least 95% CD90+ cells,
and/or
c) t least 95 CD105+ cells,
and/or
d) at least 95% HLA-class 1+ cells,
and/or
e) less than 1% CD45+ cells,
and/or
f) less than 1% CD14+ cells,
and/or
g) less than 1% CD34+ cells,
and/or
h) less than 5% HLA-DR+ cells.

9. The method of claim 8, wherein the hTERT negative and polygenic isolated mesenchymal stromal cells are (a), (b) and (c), and/or (e), (f) and (g).

10. The method of claim 3, wherein the mammalian bone marrow sample is a human bone marrow sample and the mammalian mesenchymal stromal cell is a human mesenchymal stromal cell.

11. The method of claim 1, further including the step of culturing the isolated mesenchymal stromal cells.

12. The method of claim 1, further including the step of administering the isolated mesenchymal stromal cells to a subject in need of treatment for a disease.

13. The method of claim 12, wherein the isolated mesenchymal stromal cells that are administered to the subject are administered to treat an autoimmune disease.

14. The method of claim 13 wherein the autoimmune disease is multiple sclerosis, Type 1 diabetes, rheumatoid arthritis, uveitis, autoimmune thyroid disease, inflammatory bowel disease (IBD), scleroderma, Graves' Disease, lupus, Crohn's disease, autoimmune lymphoproliferative disease (ALPS), demyelinating disease, autoimmune encephalomyelitis, autoimmune gastritis (AIG), autoimmune glomerular diseases, and graft-versus-host disease (GvHD).

15. The method of claim 14, wherein the autoimmune disease is graft-versus-host disease.

* * * * *

UNITED STATES PATENT AND TRADEMARK OFFICE
CERTIFICATE OF CORRECTION

PATENT NO. : 10,472,608 B2
APPLICATION NO. : 15/326213
DATED : November 12, 2019
INVENTOR(S) : Peter Bader et al.

Page 1 of 1

It is certified that error appears in the above-identified patent and that said Letters Patent is hereby corrected as shown below:

In the Claims

At Column 21, Claim 8, Line 16, "c) t least 95 CD105+ cells," should be replaced with
-- c) at least 95% CD105+ cells, --.

Signed and Sealed this
Twenty-first Day of January, 2020

Andrei Iancu
*Director of the United States Patent and Trademark Office*